(12) United States Patent
Conlon et al.

(10) Patent No.: US 11,931,318 B2
(45) Date of Patent: Mar. 19, 2024

(54) SMART PACK SYSTEM FOR MEDICINES

(71) Applicant: TotusRx, Inc., Longmont, CO (US)

(72) Inventors: Kevin M. Conlon, Berthoud, CO (US); Craig N. Changstrom, Loveland, CO (US); John Michael Main, Loveland, CO (US)

(73) Assignee: Swyft Inc., San Francisco, CA (US)

( * ) Notice: Subject to any disclaimer, the term of this patent is extended or adjusted under 35 U.S.C. 154(b) by 0 days.

(21) Appl. No.: 16/926,725

(22) Filed: Jul. 12, 2020

(65) Prior Publication Data

US 2021/0161769 A1    Jun. 3, 2021

Related U.S. Application Data

(63) Continuation of application No. 15/621,842, filed on Jun. 13, 2017, now Pat. No. 10,709,642.

(Continued)

(51) Int. Cl.
| | |
|---|---|
| *A61J 7/04* | (2006.01) |
| *A61J 1/03* | (2023.01) |
| *A61J 1/16* | (2023.01) |
| *A61J 7/00* | (2006.01) |
| *B65B 9/04* | (2006.01) |
| *B65B 65/08* | (2006.01) |
| *B65D 75/36* | (2006.01) |
| *G06Q 10/087* | (2023.01) |
| *G06Q 10/109* | (2023.01) |
| *G07F 17/00* | (2006.01) |

(Continued)

(52) U.S. Cl.
CPC .................. *A61J 7/04* (2013.01); *A61J 1/035* (2013.01); *A61J 1/16* (2013.01); *A61J 7/0076* (2013.01); *B65B 9/045* (2013.01); *B65B 65/08* (2013.01); *B65D 75/367* (2013.01); *G07F 17/0092* (2013.01); *A61J 2200/30* (2013.01); *B65D 2203/02* (2013.01); *G06Q 10/087* (2013.01); *G06Q 10/109* (2013.01); *G16H 20/10* (2018.01); *G16H 20/13* (2018.01); *G16H 50/30* (2018.01)

(58) Field of Classification Search
CPC .... A61J 7/04; A61J 7/0076; A61J 1/16; A61J 2200/30; A61J 1/035; B65D 9/045; B65D 65/08; B65D 75/367; B65D 2203/02; G07F 17/0092; G16H 50/30; G16H 20/13; G16H 20/10; G06Q 10/087; G06Q 10/109
USPC .................................................. 700/231–244
See application file for complete search history.

(56) References Cited

U.S. PATENT DOCUMENTS

| | | | |
|---|---|---|---|
| 5,181,189 A * | 1/1993 | Hafner | A61J 7/0481 368/10 |
| 6,411,567 B1 * | 6/2002 | Niemiec | A61J 7/0481 368/2 |

(Continued)

*Primary Examiner* — Michael Collins
(74) *Attorney, Agent, or Firm* — Toering Patents PLLC

(57) ABSTRACT

Disclosed is a blister pack smart dispensing package that has an overlay with conductors located over blister pack pockets that are broken when a user retrieves a solid medication, such as a pill, from the blister pack. The date and time that the user retrieved the solid medication from the smart pack is recorded by an electronics and communications package on the smart pack. A local communications device then receives this adherence data and transmits this data to a server, which generates a data structure containing adherence data. A blister pack overlay can be used which changes colors to indicate that the medication is about to expire, or has expired.

11 Claims, 8 Drawing Sheets

Related U.S. Application Data

(60) Provisional application No. 62/351,954, filed on Jun. 18, 2016.

(51) Int. Cl.
    *G16H 20/10*     (2018.01)
    *G16H 20/13*     (2018.01)
    *G16H 50/30*     (2018.01)

(56) References Cited

U.S. PATENT DOCUMENTS

| | | | | |
|---|---|---|---|---|
| 7,502,666 | B2* | 3/2009 | Siegel | G16H 20/13 |
| | | | | 700/242 |
| 7,552,824 | B2* | 6/2009 | Le | A61J 7/0481 |
| | | | | 206/531 |
| 9,101,530 | B2* | 8/2015 | Wilson | A61J 7/02 |
| 9,387,148 | B2* | 7/2016 | Rosenbaum | H05K 1/0286 |
| 10,709,642 | B2* | 7/2020 | Conlon | B65D 75/367 |
| 2010/0071320 | A1* | 3/2010 | Ali | B65B 5/103 |
| | | | | 700/223 |
| 2010/0089789 | A1* | 4/2010 | Rosenbaum | B65D 75/327 |
| | | | | 174/250 |
| 2010/0089791 | A1* | 4/2010 | Rosenbaum | H05K 1/0286 |
| | | | | 174/260 |
| 2013/0261794 | A1* | 10/2013 | Fauci | G16H 20/13 |
| | | | | 700/232 |
| 2014/0156064 | A1* | 6/2014 | Crawford | G16H 20/10 |
| | | | | 700/236 |
| 2016/0132661 | A1* | 5/2016 | Dixit | G16Z 99/00 |
| | | | | 53/410 |
| 2016/0253479 | A1* | 9/2016 | Fauci | G16H 20/13 |
| | | | | 700/237 |

\* cited by examiner

SMART PACK SYSTEM FOR MEDICINES

CROSS REFERENCE TO RELATED APPLICATIONS

This Application is a continuation application of U.S. patent application Ser. No. 15/621,842, filed on Jun. 13, 2017, now U.S. Pat. No. 10,709,642; which in turn claims priority to U.S. Provisional Application No. 62/351,954, filed on Jun. 18, 2016. Each of the foregoing applications is incorporated herein by reference in its entirety.

BACKGROUND OF THE INVENTION

Medicines have played an important role in the health and welfare of people throughout the world. Medicines have cured diseases, prevented infections from spreading, and reduced the instances of serious health problems. Prescription pharmaceuticals have been especially important in preventing, treating, and curing diseases.

SUMMARY

An embodiment of the present invention may therefore comprise a packet for dispensing solid medications comprising: a blister pack having a plurality of blister pockets that contain said medication; an overlay that is attached to said blister pack; geometric pattern conductors disposed on said overlay and aligned with said blister pockets when that overlay is attached to said blister pack so that said geometric pattern conductors are broken when said medication is removed from said blister pockets creating open circuits in said geometric pattern conductors; a plurality of connecting conductors disposed on said overlay that are connected to said geometric pattern conductors in a manner that provides sufficient information to detect said open circuits in said geometric pattern conductors and identify said geometric pattern conductors that have been broken; processing and storage circuitry disposed on said plastic overlay that detect said open circuits and store a time when said open circuit is detected, to create adherence data.

An embodiment of the present invention may further comprise a method of packaging solid medication in a packet and collecting adherence data indicating patient adherence to a medication schedule comprising: filling blister pockets in a blister pack with said solid medication; placing geometric pattern conductors on an overlay that are aligned with said blister pockets when said overlay is attached to said blister pack; placing a plurality of connecting conductors on said overlay that are connected to said geometric pattern conductors so that said geometric pattern conductors that have been broken can be identified; placing said overlay on said blister pack, said overlay having electronics and communication circuitry; and using said electronics and communication circuitry to detect when said geometric pattern conductors are broken by checking conductance of said connecting inductors; storing a time and date when said geometric pattern conductors are broken, to create said adherence data.

An embodiment of the present invention may further comprise an automated dispenser that dispenses medications to a user comprising: a package containing medications comprising: a blister package containing said medication in blister pockets; processing, storage, and communication circuitry disposed on an overlay that covers said blister pockets, said processing storage, and communication circuitry containing identifying said medication; communication electronics disposed in said automated dispenser that receives prescriptions for said medication and receives said data identifying said medication from said processing, storage and communication circuitry disposed on said overlay; a processor that generates control signals that control a card reader that reads debit and credit cards, a display screen to prompt said user, a labeler that generates a label containing information identifying a patient taking said medication and instructions for taking said medication, and a dispenser that dispenses said medication.

An embodiment of the present invention may further comprise a method of automatically dispensing medication to an authorized user of an automated dispenser comprising: packaging said medication in a blister package having processing, storage and communication circuitry disposed on an overlay of said blister package that contains data that identifies said medication packaged in said blister package; communicating said data identifying said medication from said blister package to said automated dispenser; receiving prescription data for a patient at said automated dispenser; programming said blister package with said prescription data; generating a patient label identifying said patient for said medication and instructions for use of said medication; applying said patient label to said blister package; verifying that a user of said automated dispenser is said authorization user of said automated dispenser; dispensing said medication to said authorized user.

An embodiment of the present invention may further comprise a communication system that communicates adherence data, indicating adherence by a patient to a medication schedule, for access by authorized individuals on a network comprising: a smart dispensing package comprising: a blister pack having a plurality of blister pockets that contain medication; a plastic overlay that is attached to said blister pack; a plurality of geometric pattern conductors disposed on said plastic overlay that are aligned with said blister pockets when said overlay is attached to said blister pack do that said geometric pattern conductors are broken when said medication is removed from said blister pockets, creating an open circuit; a plurality of connecting conductors disposed on said overlay that are connected to said geometric pattern conductors in a manner that provides sufficient information to detect an open circuit in each of said geometric pattern conductors so that open circuits in each of said geometric pattern conducts can be identified; processing and storage circuitry disposed in said plastic overlay that detects said open circuits and stores a time when said open circuit is detected, to create adherence data; communication circuitry disposed on said plastic overlay and connected to said processing and storage circuitry that transmits said adherence data on an antenna disposed in said plastic overlay; a handheld communicator that receives said adherence data from said smart dispensing package and transmits said adherence data to a network for storage and access by said authorized individuals.

An embodiment of the present invention may further comprise a method of transmitting adherence data from a packet that contains solid medications comprising: packaging said medication in blister pockets of a blister package; detecting an opening of a blister pocket by detecting conductance of a plurality of conductors disposed on an overlay that cover said blister pockets; recording a time when said blister pocket is opened to create adherence data; transmitting said adherence data from said packet to a handheld communicator; transmitting said adherence data from said handheld communicator to a network that is accessible by authorized individuals.

DETAILED DESCRIPTION OF THE EMBODIMENTS

Figure 1:
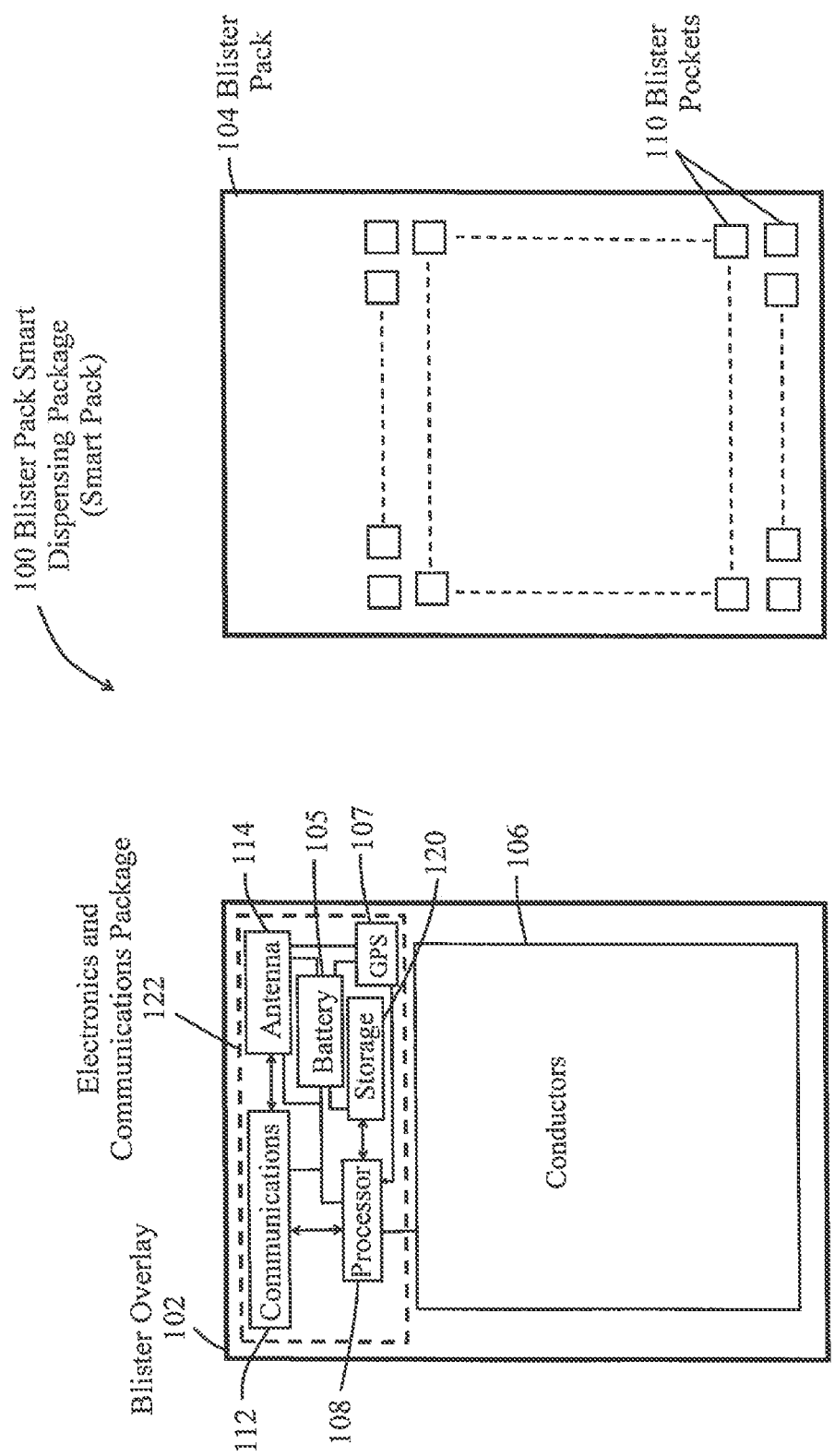
FIG. 1 is a schematic block diagram of an embodiment of a blister pack smart dispensing package (smart pack).

FIG. 1 is a schematic block diagram of an embodiment of a blister pack smart dispensing package 100 that is referred to herein as a "smart pack 100." As disclosed in FIG. 1, the smart pack 100 consists of a blister pack 104 that has a plurality of indentations or blister pockets 110 that are arranged and sized to carry solid medications, such as one or more pills, gummies, etc., referred to herein as "pills." The pills may be prescription or non-prescription medications, supplements, or other substances that may be desirable to ingest on a periodic basis. For example, vitamin or mineral supplements can be used with the smart pack 100, illustrated in FIG. 1. The blister pack 104 can be fabricated from any standard material that meets FDA regulations for materials suitable for use with pills including many plastics and is capable of deformation to form the blister pockets 110.

As also illustrated in FIG. 1, the blister overlay 102 has the same form and size as the blister pack 104. The blister overlay 102 may have a contact adhesive coating on a lower surface, so that when the blister overlay 102 is placed on the blister pack 104, it becomes secured to the blister pack 104. Other standard methods of securing the blister overlay 102 to the blister pack 104 can be used, such as a UV sealing, a heat responsive adhesive, or other adhesives. The electronics and communications package 122 is located over a portion of the blister pack 104 that does not have blister pockets 110, such as illustrated in the embodiment shown in FIG. 2. The conductors 106 are laid out over the area where the blister pockets 110 are disposed, as also shown in FIG. 2.

Referring again to FIG. 1, the electronics and communication package 122 includes a processor 108 that is connected to the conductors 106. The processor 108 transmits signals periodically to the conductors 106 to determine conductivity and thereby determine if a portion of the blister overlay 102 has been punctured to remove a pill disposed in a blister pocket 110. When it is determined that there is a lack of conductivity (open circuit) of the conductors adjacent to a blister pocket 110, indicating that a pill has been removed from a blister pocket 110, the time and date is stored in storage circuitry 120. The processor 108 then transmits this information (referred to herein as "adherence data") to the communications circuitry 112, which causes the adherence data to be transmitted via antenna 114, to a local receiver. In one embodiment, a mobile phone, pad computer, or other device, connects with the electronics and communication package using a near field communication (NFC) signal when a link is established. The communications circuitry 112 requests adherence data from processor 108, which then retrieves the adherence data from storage 120. The adherence data indicates whether a patient has adhered to the medication schedule that has been prescribed for that medication. The processor 108 then transmits the adherence data retrieved from storage 120 to the communications packet 112 and to the antenna 114. The adherence data is then received by the NFC device, or other communication device, such as a mobile phone, as explained in more detail below. A battery 105 powers the electronics and communicator package 122. A GPS receiver 107 may also be included in the electronics and communications package 122. GPS receiver 107 is connected to antenna 114 and receives satellite data, determines a physical location of the smart pack 100 and transmits the location data to processor 108.

Figure 2:
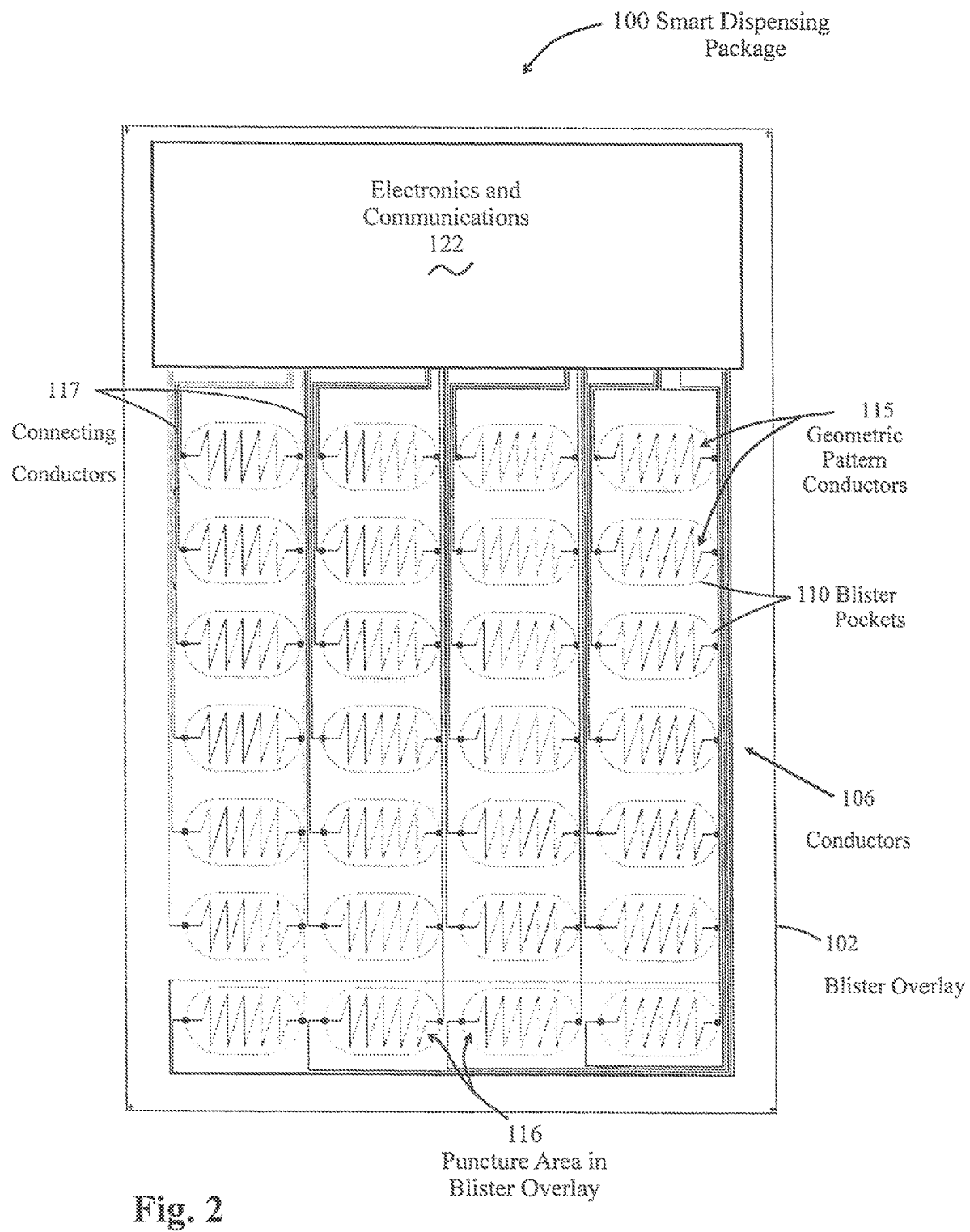
FIG. 2 is a detailed view of an embodiment of a smart dispensing package.

FIG. 2 is a schematic illustration of the smart dispensing packet 100 showing the conductors 106 that are disposed on the blister overlay 102. The conductors may be deposited on the blister overlay 102 using a conductive ink, or other conductive material. As illustrated in FIG. 2, the conductors 106 are spread out in a geometric pattern, creating geometric pattern conductors 115 that are positioned over the puncture area 116 of the blister overlay, so that puncture of the blister overlay 102 to retrieve medication from a blister pocket 110 (FIG. 1) will result in the geometric pattern conductor 115 being broken and disconnected from the circuit, creating an open circuit. The lack of a conductive path for that particular row and column for the blister pocket 110, where the open current is located, is determined by the electronics and communication circuitry 122, and the time and day, and in some cases the location of the smart pack 100, is recorded by the electronics and communication circuitry 122. When there is a puncture and a resultant open circuit, it is assumed that the patient punctured the blister overlay 102, removed, and consumed the medication. The time and day and in some cases the location that this occurred is referred to as "adherence data" since the data indicates whether the patient has adhered to the prescribed medication schedule. This adherence data is stored in the electronics and communication circuitry 122. The blister overlay 102 is made from a thin plastic material, which allows a user to puncture the blister overlay 102 to gain access to the pills stored in a blister pocket 110. The blister overlay 102 is, however, sufficiently strong to prevent accidental puncture and disruption of the conductors 106 on the blister overlay 102. Conductive ink, which forms a conductor, can be applied in several different ways. For example, conductive ink can be screened onto the blister overlay 102, using standard off-set printing techniques or standard screening techniques. In addition, the conductive ink can be applied with a plotter using inkjet technology. Other methods can also be used. It is important that the ink adhere well to the blister overlay 102, so that a material should be used for the blister overlay 102 that allows for good adhesion of the conductive ink. The overlay materials may be foil materials that are coated with an insulated plastic, a paper material, various plastics, biodegradable materials, plant based materials that change color over time such as disclosed herein, heat sensitive materials, UV sensitive materials, linear or bidirectional aligned molecular material or virtually any material that can be printed and broken using standard finger pressure. Single or multiple layer overlay configurations consisting of either a single or multiple materials can also be used. Printed electronics can be used in multiple layer configurations to prevent the accidental removal of a conductor as a result of abrasion during handling of the smart pack 100. The materials used should be designed to have a selective bursting pressure which allows a user to access a blister pocket 110 using standard finger pressure. In addition, the overlay may have reinforced areas that are not aligned with the blister pockets 110 so that the bursting pressure adjacent the blister pockets 110 is much less than other portions of the blister overlay 102. Polypropylene and polyethylene are two example materials that may be used for the blister overlay 102. The conductive ink can be made from various materials including powder, liquid or plant based materials. The conductive ink can be curable with heat, UV light or various chemical processes. The conductive ink can also cure simply by drying. The conductive ink is flexible and has the ability to conduct when subjected to fluctuations such as bending of the blister overlay 102. The conductive ink can be formulated to change color or shades upon the occurrence of certain conditions. For example, the conductive ink may initially be invisible to minimize the visual footprint of the printed electronics while retaining the conductive functionality of the conductive ink. A color change or shading change may then occur to indicate a change of state or environmental change such as when the package contents have expired. For example, the conductive ink or other inks placed on the overlay can indicate that the package contents, i.e. the medications or other materials stored in the blister pack, have expired.

The conductors 106 may comprise geometric pattern conductors 115 such as the zigzag geometric pattern conductors illustrated in FIG. 2. Of course, any geometric pattern can be used for the geometric pattern conductor 115. The conductors 106 also include the connecting conductors 117 that connect the geometric pattern conductors 115 to the electronics and communication circuitry 122. The connecting conductors 117 may be laid out in rows and columns or other layout that allows identification of each geometric pattern conductor 115 that is broken. In other words, the connecting conductors 117 are connected to the geometric pattern conductors 115 in a manner that allows each of the geometric pattern conductors 115 to be individually identified as to the location of the geometric pattern conductor 115 on the blister overlay 102 so that the blister pocket 110 that has been accessed can be identified using conductance to identify the rows and columns of each geometric pattern conductor 115, that has been broken. The use of series connected resistive conductors to reduce the number of connecting conductors, such as disclosed in U.S. Pat. No. 8,960,440 and U.S. patent application publications US 2015/0286852, US 2015/0148947, US 2010/0089791, US 2017/004284 and PCT application WO 2017/062464 does not allow identification of individual blister pockets such as blister pocket 110. The identification of which blister pocket has been opened allows identification of the medication that has been accessed by the patient. In this manner, there is no confusion as to the specific blister pocket that has been opened or number of blister pockets 110 that have been accessed, and the specific date and time which these blister pockets have been accessed. As such, a clear chain of possession of each of the pills of the medication can be established.

In addition, the electronics in communication package 122 which is placed on the blister overlay 102 is operated by battery 105. Using resistive elements to determine which blister pocket has been accessed uses substantially more energy than simply checking the conductance of the conductors 106. Accordingly, the layout, such as illustrated in FIG. 2 in which each geometric pattern conductor 115 can be checked for conductance because each geometric pattern conductor 115 is connected to a connecting conductor 117 is a much more efficient manner of determining the location of a broken geometric pattern conductor 115 compared to using resistive elements.

Furthermore, both the geometric pattern conductors 115 and the connecting conductors 117 can be easily and inexpensively printed with conductive ink as described above. The inexpensive processes for printing the conductive ink such as screening, ink jet printing, off-set printing and the other techniques described as well as other inexpensive techniques reduces the manufacturing costs of the smart dispensing package 100. The smart dispensing package 100 then becomes a disposable package that is manufactured by highly automated techniques to allow mass-production of the smart dispensing package 100. The electronics and communications circuitry 122 can be attached to the blister overlay 102 using adhesives or other bonding materials that firmly secure the electronics and communications circuitry 122 to the overlay 102. Automated pick-and-place robots can accurately place the electronics and communication circuitry 122 on the blister overlay 102. In addition, the conductors 106 can be accurately aligned with the electronics and communications circuitry 102 using standard edge detection techniques. Electronics and communications circuitry 122 includes an antenna 114 (FIG. 1) for transmitting and receiving information on the blister pack smart dispensing package 100. The antenna can be printed using conductive ink using the various techniques disclosed herein.

Figure 3:
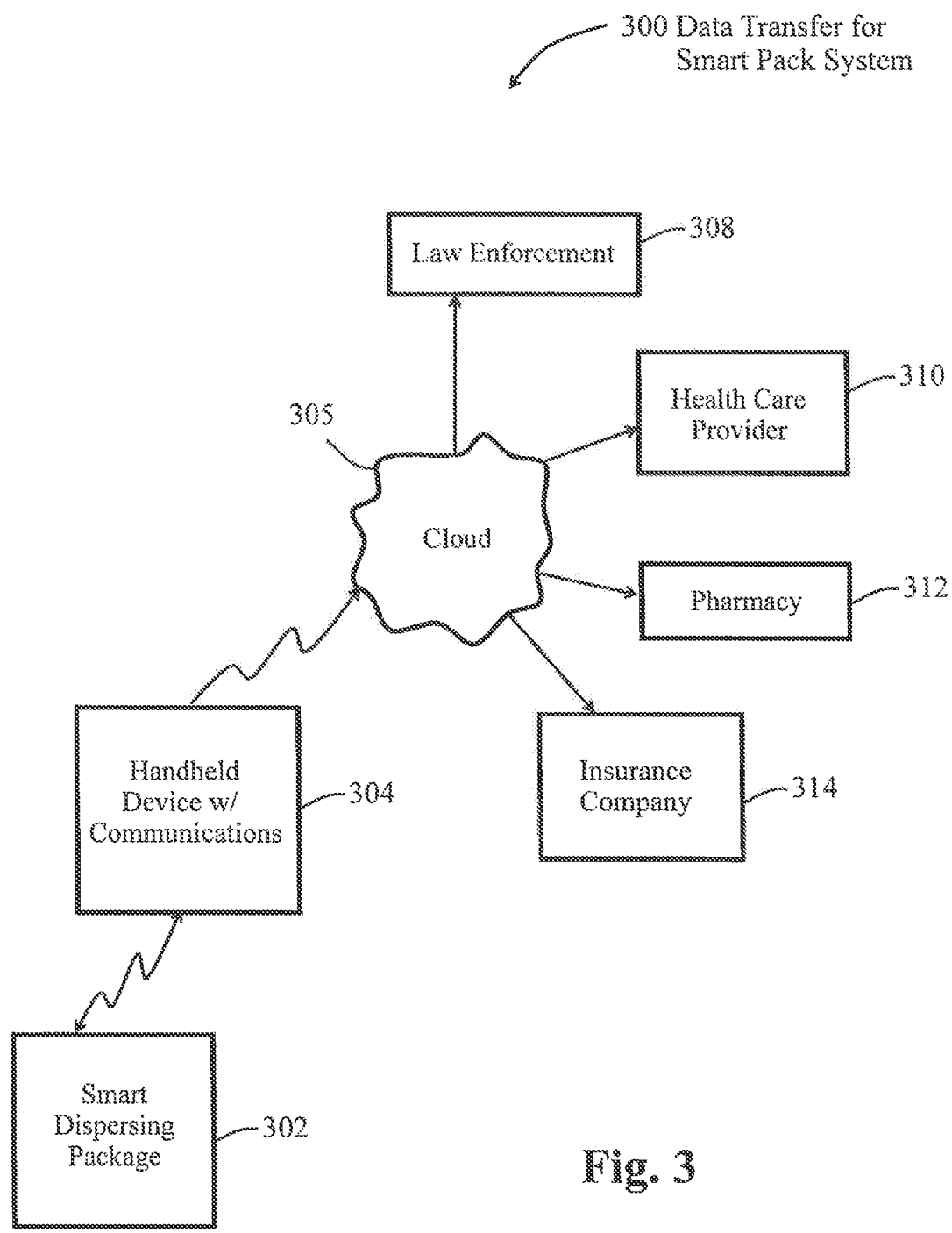
FIG. 3 is a schematic block diagram of the data transfer structure for the smart pack system.

FIG. 3 is a schematic block diagram illustrating an embodiment of a system for data transfer of data generated by the smart dispensing package 302. As illustrated in FIG. 3, the smart pack, or smart dispensing package 302, collects and stores adherence data, together with information regarding the patient as described above. A handheld device, such as a cell phone, pad computer, or other device, that includes a communications system, links to the smart dispensing package 302. When a communication link is established, the smart dispensing package 302 retrieves adherence data and medical identification data for the patient from storage 120 (FIG. 1) and transmits the adherence data via communications package 112 and antenna 114 to the handheld device 304.

The handheld device 304 of FIG. 3 can comprise any device that can establish a link to smart pack 302 and retransmit data, and does not have to be handheld. For example, fixed communications systems may be located at various locations, such as in homes, public buildings, malls, doctors' offices, hospitals, and other locations that can perform the same functions as the handheld device 304 and, for purposes of this application are all referred to as handheld devices. The handheld device 304 may use any number of different protocols, including a near field communication protocol, Bluetooth, Wifi, various RFID protocols, zigbee, WIMAX, or other communication protocol. For ease of disclosure, all of these communication devices are referred to hereinafter as "handheld devices" even if they are stationary devices.

The handheld device of FIG. 3 then retransmits the adherence data to the cloud 305. The cloud 305 consists of servers and storage for storing adherence data for each patient, which can then be accessed, via a secure password, or other security techniques such as by encryption, by authorized individuals, such as law enforcement 308, healthcare providers 310, pharmacies 312, or insurance companies 314. The adherence data can be used to create a patient accountability score or adherence score which can be used for a number of different purposes. Patient accountability data is used to create an accountability score, or patient accountability, that indicates how accountable a patient has been in adhering to the regimen of taking the medication. An accountability score can be generated in various different ways. For example, a patient accountability score can be generated based upon the percentage of the times which the patient has taken the medication. As an example, if a patient is only taking the medication 50% of the time, the patient score can be 50. If the patient takes the medication 100% of the time, the score would be 100. The scoring entity can also modify the score if the patient takes the medication late. In this manner, a patient accountability score can be created in accordance with the specific information that is of importance to the entity that designs the patient accountability score.

Law enforcement may use the adherence data and location data to determine if there has been a misuse of a controlled substance, such as opioids. A healthcare provider 310 may use the patient accountability score to determine the efficacy of the treatments to the patient and to modify a treatment program for the patient. Pharmacies and automated dispensers may use the adherence score for automated restocking of inventory using an automated inventory program. Insurance companies 314 may set the price of health insurance based upon the patient accountability score. Insurance companies and healthcare providers may use the patient accountability score to encourage the patient to more carefully adhere to the schedule for taking medicines.

Figure 4:
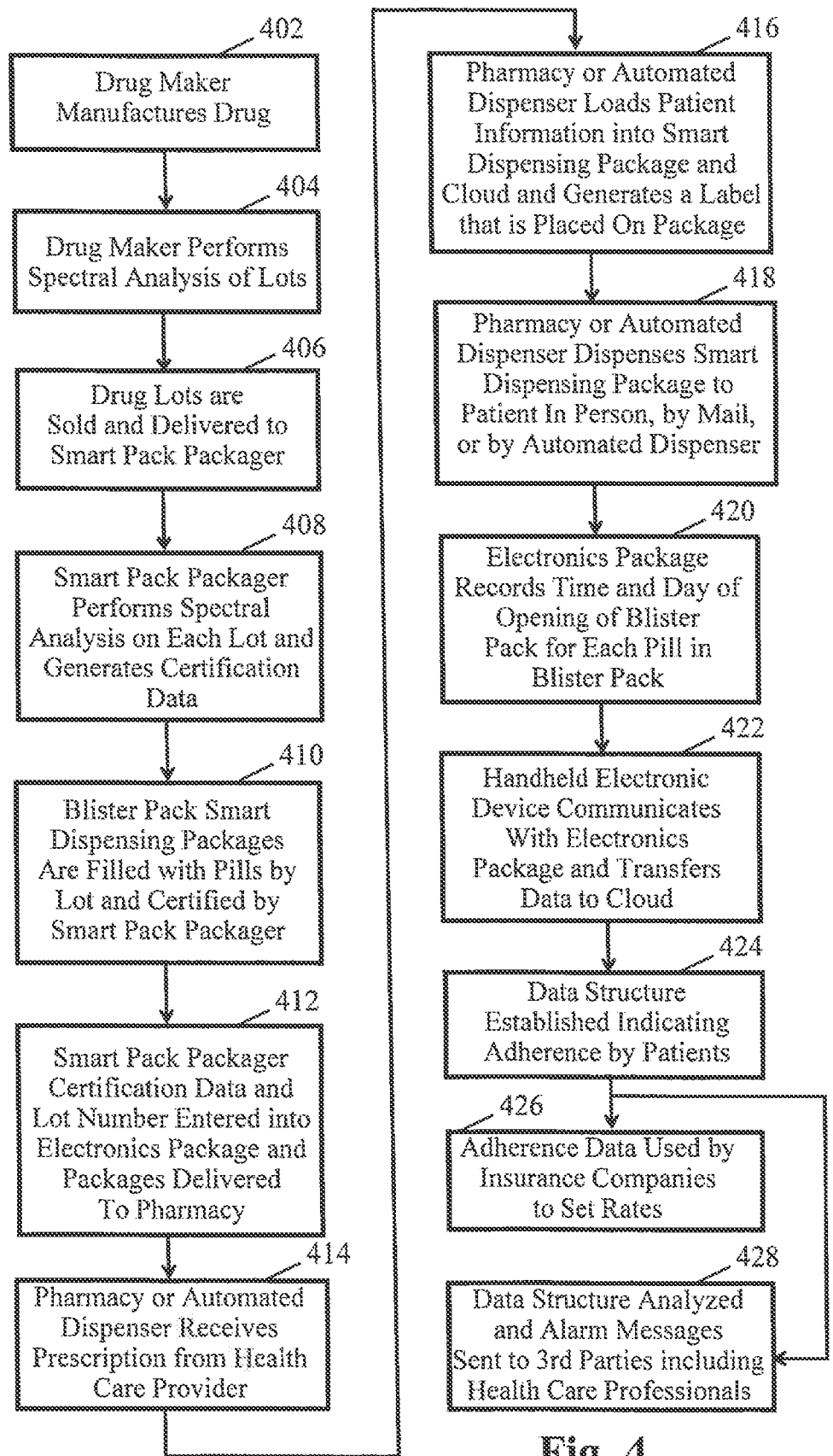
FIG. 4 is a flow diagram of the distribution and data collection process for an embodiment of a smart pack system.

FIG. 4 is an embodiment of a distribution and data collection process 400 using the various embodiments of the smart pack system illustrated in FIGS. 1 through 10. As illustrated in FIG. 4, the drug maker originally manufactures the drug at step 402. Currently, drugs are being manufactured around the world. Some drug manufacturers produce better drugs than others. In addition, there are a number of instances of counterfeit drugs being manufactured and sold on the open market. Under U.S. law, drug manufacturers must provide data for each lot of drugs it has manufactured, in an effort to prevent the sale of counterfeit drugs or low quality drugs. However, sometimes this data is falsified, resulting in patients receiving low quality or counterfeit medications. If this is discovered, recalls usually occur by manufacturing lot. When filling prescriptions, pharmacies may fill the prescription by drawing from two or more lots to completely fill the prescription. As such, filled prescriptions may include pills that are mixed from different lots. If a recall is issued for a particular lot, the entire filled prescription will have to be recalled, resulting in a waste of medications that may be perfectly fine, assuming that the pharmacy has even kept records of which lots were used to fill the prescription. This can be an expensive process, since some medications can be quite costly. Further, the expiration of the medications from different lots may be different. The expiration date must be set for the expiration date of the lot which has the earliest expiration data, which can also result in a waste of medication. Further, U.S. law requires that a chain of custody be established from the drug manufacturer all the way to the end user. As indicated above, pharmacies may, or may not, actually record which lots of a medication were used to fill a prescription. As a result, the chain of custody of each lot of medication is not established, which is a violation of U.S. drug regulations.

At step 404, of FIG. 4, the drug maker performs a spectral analysis of each of the lots of medications and provides the drugs and data to a drug wholesaler. If each of the pills in the blister pockets has undergone spectral analysis, and that data is saved, a detailed record of the strength or efficacy of the medications taken by a patient can be determined by a healthcare provider or other authorized individual. The drug wholesaler then sells the drugs by lot and the lots can be delivered to a smart pack packager, at step 406. In order to overcome the problems of mixing lots and detecting poor quality drugs, the smart pack packager performs its own spectral analysis of each lot and generates certification data. In this manner, the smart pack packager can certify the efficacy and strength of the drugs and, from that data, can calculate expiration dates and medication strength. In this manner, falsified, or otherwise incorrect, data from a drug manufacturer is detected and a certification is then made by the smart pack packager regarding the efficacy of the drugs. At step 410, the blister pack smart dispensing packages are filled with pills by lot, with the certification provided by the smart pack packager.

Since the smart packs illustrated in FIGS. 1 and 2 can be manufactured to hold a different number of pills, there is little waste in ensuring that each smart pack only includes a single lot of medication. For example, some smart packs may only have eight or ten blister pockets, while others may have up to 50 blister pockets. Mixing and matching the blister packs for a particular medication allows the blister pack packager to effectively use medications from a single lot in each blister pack with little or no waste.

At step 412 of FIG. 4, the smart pack packager certification data and lot number data are entered into the electronics and communication package 122 together with the identifying information of the drug, and the smart packs are then delivered to a pharmacy 312, or automated dispenser 600 (FIG. 6), at step 412. In some cases, the smart pack packager may be a pharmacy. At step 414, the pharmacy 312, or automated dispenser 600, receives the prescription from the healthcare provider for a particular individual. A secure communication link between the healthcare provider 310 and the automated dispenser 600 is established. In addition, secure authorization codes are also established to prevent any fraud in loading a prescription into an automated dispenser.

At step 416 of FIG. 4, the pharmacy 312, or the automated dispenser 600, loads the patient information into the smart pack 100 and stores this information as to the prescription, the serial number of the smart pack 100, and other information, on a server/storage on the cloud. The pharmacy 312, or automated dispenser 600, then generates a patient label 506, which is placed on the box 502 (FIG. 5) containing the smart pack 100.

At step 418 of FIG. 4, the pharmacy 312, or automated dispenser 600, dispenses the smart pack package 500 (FIG. 5) to the user in person, by mail, or in the case of an automated dispenser 600, at the location of the automated dispenser 600. At step 420, the smart pack 100 has been distributed to the user and the electronics and communications package 122 on the smart pack 100 records the time and day; and possibly the location, of opening of the smart pack 100 for each pill in the smart pack 100. At step 422, a handheld electronic device, such as a mobile phone, pad computer, or other communication device, that includes a communications package, such as near field, communications, Bluetooth, or other communication protocol, as described in more detail above, communicates with the electronics and communication circuitry 122 on the smart pack 100 and transfers data stored in the electronics and communication package 122 to designated servers and storage on the cloud. The handheld electronic device, or other device, transfers the information to the cloud when it is connected by Wifi, or other connection, to the cloud. At step 424, a data structure is established, which indicates adherence of the patient to a medication schedule. At step 426, the adherence data is used by insurance companies to set rates and for other uses. At step 428, the data structure is analyzed and alarm messages can be sent to third parties, including healthcare professionals, if a patient has not taken needed medication within a certain period.

Figure 5:
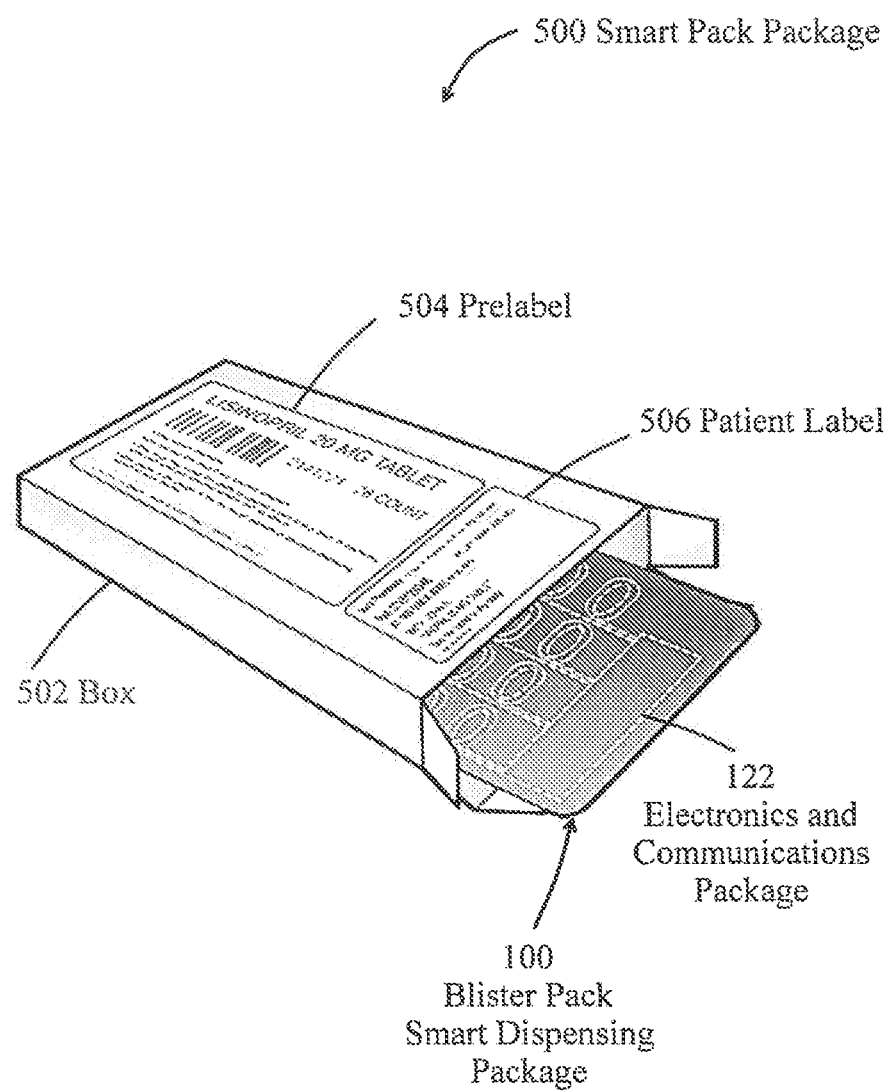
FIG. 5 is an illustration of an embodiment of a smart pack package for the smart pack system.
Figure 6:
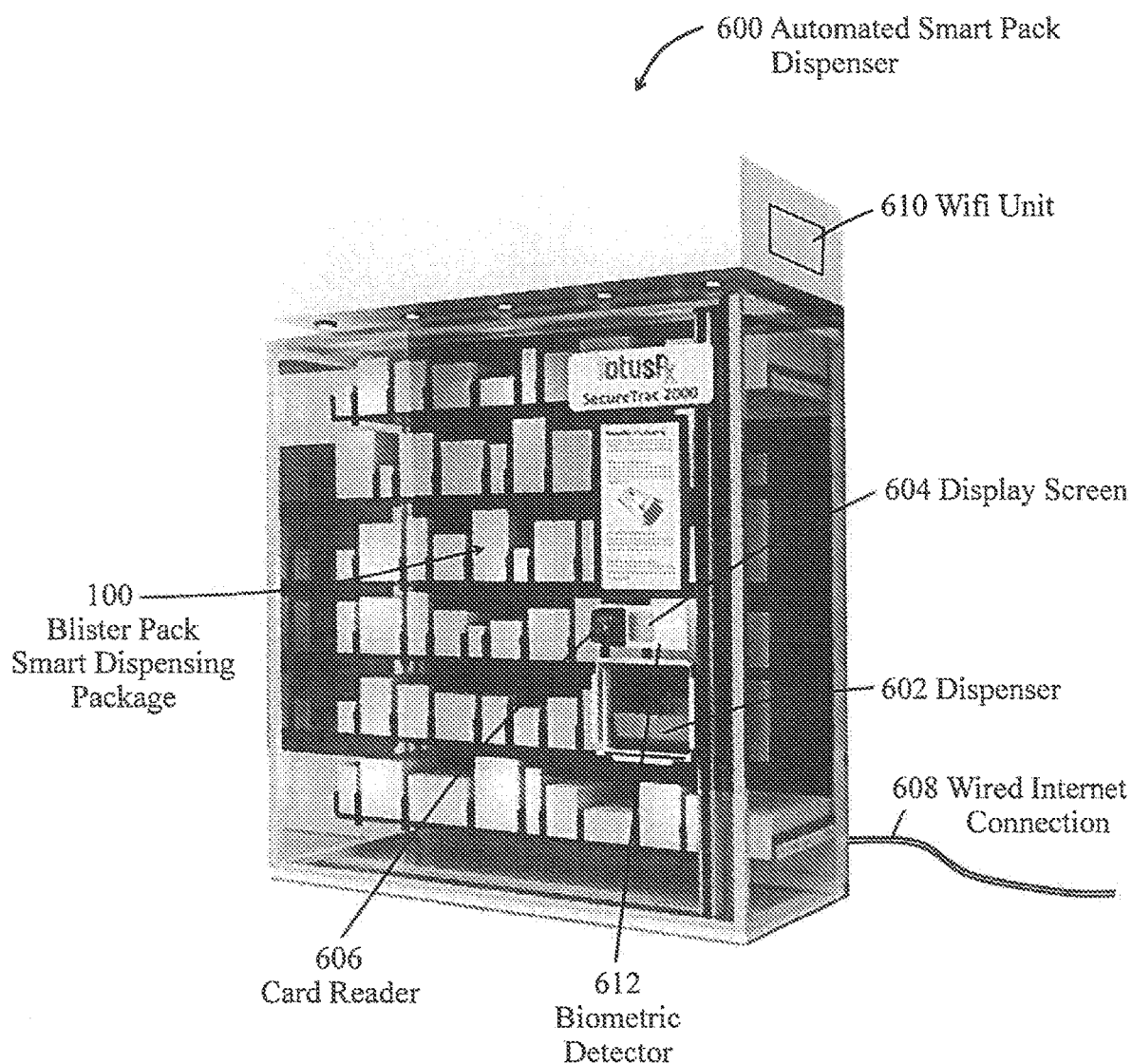
FIG. 6 is a schematic illustration of an embodiment of an automated smart pack dispenser.

FIG. 5 is a schematic illustration of the smart pack package 500 for the smart pack system. As illustrated in FIG. 5, smart pack package 500 includes a box 502 having a prelabel 504. The prelabel has all of the identifying information for the medication included in the blister pack smart dispensing package 100. In the example shown in FIG. 5, the medication is 20 mg tablets of Lisinopril, a blood pressure medicine, which is shown at the top of the prelabel 504. The prelabel also includes a bar code, which identifies the medication and a serial number that is associated with the blister pack smart dispensing package 100. The box 502 also includes a patient label 506. Prior to dispensing the package illustrated in FIG. 5, the pharmacy, or automated dispensing device, prints a patient label 506 that identifies the patient and provides instructions on how to take the medication. The automated smart pack dispenser 600, illustrated in FIG. 6, is capable of printing a patient label 506 from the information provided to the automated dispenser 600 by the healthcare provider 310. In addition, the pharmacy 312, or automated smart pack dispenser 600 (FIG. 6) loads the patient data into the blister pack smart dispensing package 100 using the electronics and communication package 122 disposed on the blister pack smart dispensing package 100. Again, the electronics and communications package 122 may use near field communication techniques or other communication protocols to transmit and receive patient information. A wireless communication system can be used by the pharmacy 312, or an automated smart pack dispenser 600, to load the patient data into the blister pack smart dispensing package 100.

FIG. 6 is a schematic illustration of an embodiment of an automated smart pack dispenser 600. The automated smart pack dispenser 600 has a secure communications link to either a pharmacy 312 or healthcare provider 310, so that either a pharmacy 312 or healthcare provider 310 can provide patient prescription information to the automated smart pack dispenser 600. For example, the automated smart pack dispenser 600 may be connected via a secure T1 line to a central office and may send and receive secure communications that are encrypted. In another embodiment, the automated smart pack dispenser 600 may have a Wifi or wired Internet connection, such as Wifi unit 610, or wired Internet connection 608 and encrypted data can be communicated over the Internet. The automated smart pack dispenser 600 can therefore receive prescription data and dispense prescriptions automatically to authorized individuals. Highly controlled prescriptions, such as opioids, can also be dispensed through the automated smart pack dispenser 600, through the use of a biometric detector 612. The biometric detector 612 includes a sensor for sensing biometric information regarding the patient, such as fingerprints, iris detection, retinal detection, or other biometric information. For example, facial recognition may be used and compared to a stored picture of a patient. Typical iris or retinal detectors require the user to stare into the detector to identify the patient as a result of the unique character of the iris or retina. Of course, the biometric data must be transmitted to the automated smart pack dispenser 600 from a healthcare provider, or other source, so that the automated smart pack dispenser 600 can compare the detected biometric data with the stored biometric data. Government IDs can also be used to identify a patient.

The automated smart pack dispenser 600 of FIG. 6 contains the packages of medications such as box 502, as illustrated in FIG. 5, which contains the blister pack smart dispensing package 100 that includes the electronics and communications package 122, the prelabel 504 and the patient label 506. When a prescription is received by the automated smart pack dispenser 600, the patient is prompted to insert a credit or debit card in the card reader 606, to authorize the transaction. Communication electronics 706 (FIG. 7) disposed within the automated smart pack dispenser 600, of FIG. 6, then generates an encrypted wireless signal that is directed to a specific blister pack smart dispensing package 100, located in the automated dispenser 600. In other words, the signal generated by the communication electronics 706 is encoded for a specific box of medication contained in the automated dispenser 600 so that the electronics and communication package 122 (FIG. 5) for that specific box of medication can be programmed with the prescription information for the patient purchasing the medication. The smart pack 100 is then programmed with the prescription information for that patient. Simultaneously, a labeler 716 (FIG. 7) generates a patient label 506 (FIG. 5), which is placed on the box 502 (FIG. 5) for the designated blister pack smart dispensing package 100 that has been designated for that patient in the automated smart pack dispenser 600. That package is then dispensed through dispenser 602 to the patient. If the prescription is a controlled medicine, such as an opioid, the patient must identify themselves by using the biometric detector 612 prior to dispensing the package to the patient.

Figure 7:
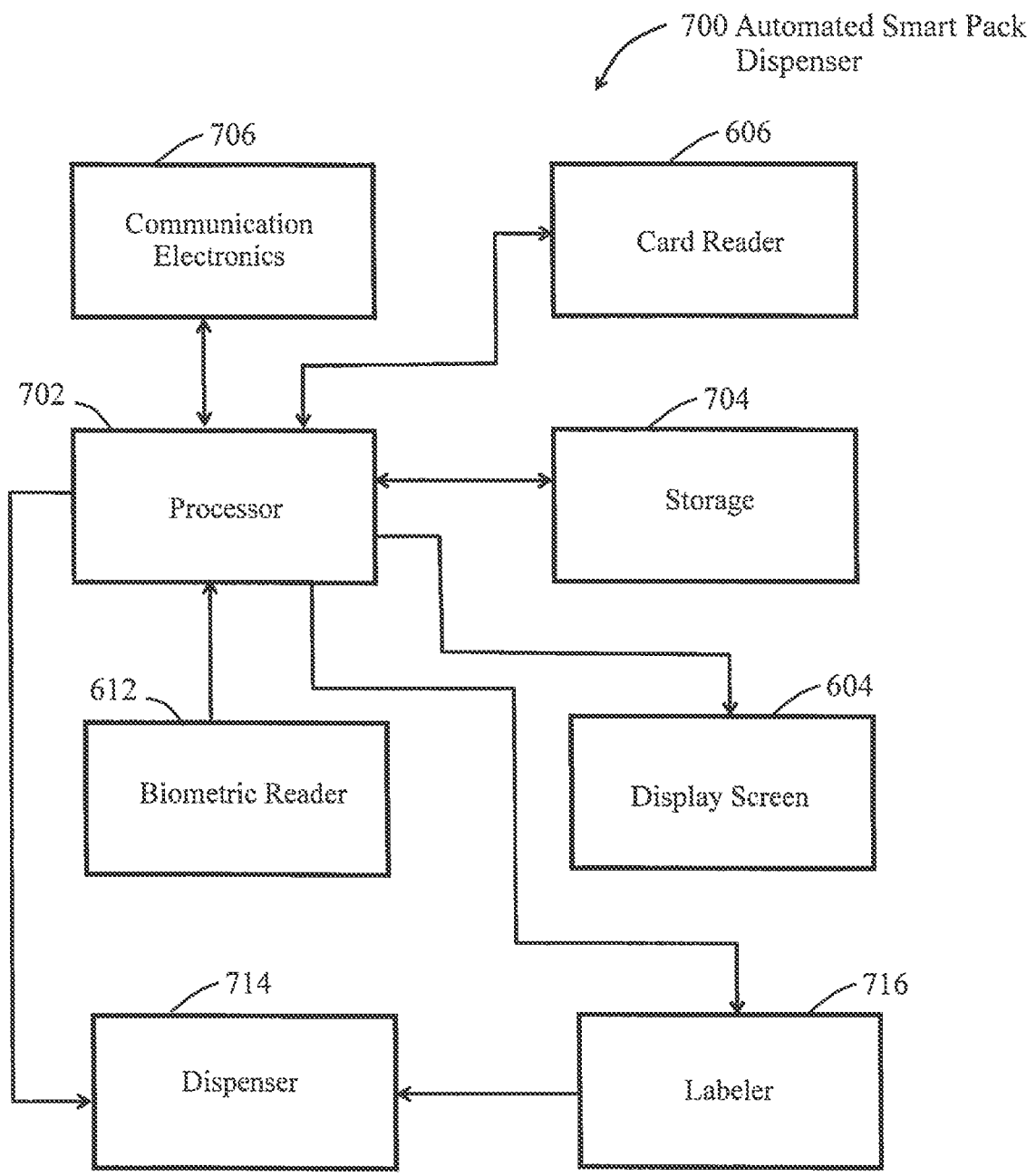
FIG. 7 is a block diagram of an embodiment of the electronics structure of an automated smart pack dispenser.

FIG. 7 is a schematic block diagram of various electronic components of the automated smart pack dispenser 700. As illustrated in FIG. 7, a processor 702 is programmed to control the various components illustrated in FIG. 7. Communications electronics 706 receives secure transmissions from a pharmacy or healthcare provider relating to prescriptions to be dispensed by the automated smart pack dispenser 700. The prescription data is then forwarded to the processor 702, which stores the prescription data and generates information regarding the patient and the prescription to be dispensed, which is displayed on display screen 604. The processor then displays a message on the display screen 604 to have the user of the automated smart pack dispenser 700 insert a debit or credit card into the card reader 606. A government ID can also be read by card reader 606 to identify the user of the automated dispenser 600. The processor transmits the card information via the communication electronics 706 via the Internet, or a secured T1 line, to a bank or card company for authorization. Authorization data is then received from the bank or card company via the communication electronics 706. The processor 702 then generates information for the patient label 506 (FIG. 5) from the patient data in the storage 704. If the prescription calls for a controlled medication, such as an opioid, the processor 702 generates a signal for the display screen 604 that instructs the user to use the biometric reader 612. For example, a patient may be directed to look into the biometric reader 612 to obtain an iris or retinal scan. In another embodiment, a patient may be asked to place a finger, or a hand, on a fingerprint or hand reader for verification. Of course, if the prescription is not a controlled medication, such as an opioid, a biometric reader is not required, since any authorized adult can sign for the medication. Once the payment has been authorized and the patient label 506 has been applied to box 502 (FIG. 5), the dispenser 714 dispenses the box 502.

Figure 8:
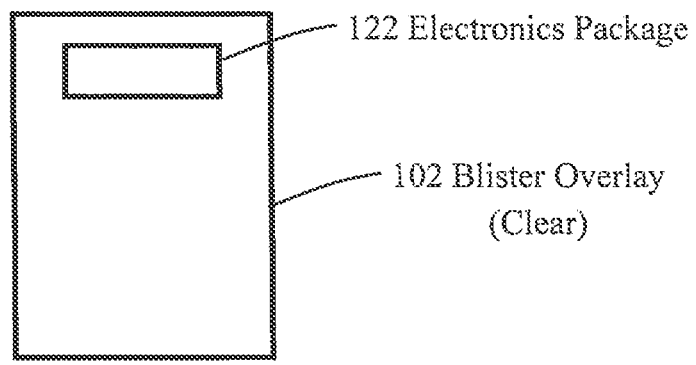
FIGS. 8-10 are schematic illustrations of an embodiment of a smart pack that changes colors or shades as the medications in the smart pack approach expiration and reach expiration.

FIG. 8 is a schematic illustration of the blister overlay 102. The blister overlay 102, as illustrated in FIG. 8, contains compounds that age over time. These compounds are plant based material that change color or shading over time. The color and shading is based upon oxidation of these plant based materials that change color and shade as a result of oxidation. The blister overlay 102 is manufactured to change color or shading over a specific time period. The blister overlay 102, illustrated in FIG. 8, is a newly manufactured overlay that is clear. The time period over which the color change occurs in the blister overlay 102, corresponds to the expiration date of the medication enclosed in the smart pack 100 which can include drugs, supplements, pharmaceuticals, nutraceuticals, orals, solids, liquids, powders and gels, as set forth above. Orders are dispensed by pharmacies and automated dispensers based upon color change tables which have a corresponding expiration date for the contained contents. This information is also loaded into the electronics and communication package 122 and stored in the storage 120, as illustrated in FIG. 1. As such, the color or shade change that occurs in the blister overlay 102 is time based and duration specific. The color or shade change is tied to the drug expiration date so that blister overlays 102 are matched with specific lots of drugs that have a corresponding expiration date. In this manner, the potency and strength and the corresponding expiration date can be matched with the proper blister overlay 102 so that the color change or shading is a visual indication of the potency or viability of the drug. Of course, inhibitors can be used which inhibit the process of color and shade change to slow the process of color and shade change. Further, accelerators can be added to the process to speed up the color and shade changing process. Some of these inhibitors and accelerators use processes for changing the oxidation rate of the materials that cause the color and shade change. In some cases, the price of the contents of the smart pack 100 can be adjusted and the price can be based upon the potency of the contents of the smart pack 100. In that regard, the price may be reduced for a drug that is less potent. For example, it is known that antibiotics lose potency over time. After several years, the potency may be reduced by a percentage of the original potency. Although the drug is still effective at a reduced potency, the entity selling the drug may wish to reduce the price. The color change and shading can be automatically detected using photoelectric devices, optical sensors, CCD arrays, photographic techniques, and other light sensing techniques. These detected values of color and shade changes can then be stored in the electronics and communication package 122 in storage 120. In this manner, the smart pack 100 can communicate information relating to potency of the contents of the smart pack 100 and the status of the color/shade change without physically inspecting the package. The stored data can provide information as to whether or not the contents of the smart pack 100 can be used. For certain products, not only does the efficacy of the product change, but some products should not be used after an expiration date. If a product is determined to be in an unsafe range, notifications and certain protocols can be used to contact the user and the proper authorities to confiscate and destroy the product. These communication protocols can be either automatic or manually performed by proper authorities.

As also illustrated in FIG. 8, in the process of manufacturing the blister overlay 102, the electronics package 122 is deposited, or placed by various methods, on the blister overlay 102. In one embodiment, a silicone substrate can be bonded directly onto the blister overlay 102. Conductive ink can be used to connect the various components and create the conductors 106 (FIG. 1), as illustrated in FIG. 2.

Figure 9:
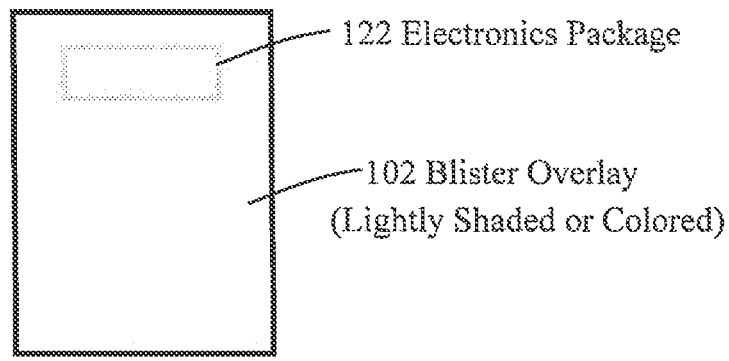

FIG. 9 is a schematic illustration of the blister overlay 102 that has become shaded or has changed colors as a result of the expiration of a certain time period. In other words, the blister overlay 102 begins to change colors, as illustrated in FIG. 9, after a period of time, indicating that the expiration period for the medications in the smart pack is approaching. When the blister overlay 102 is manufactured, the combination of compounds used in the blister overlay determines the time when the blister overlay 102 starts to change colors, or becomes shaded. The blister overlay is matched with the expiration date of a particular lot of medications that has an expiration date corresponding to when the blister overlay 102 changes colors. The blister overlay 102 is then used with a blister pack 104 (FIG. 1) containing pills that have a matching expiration date.

Figure 10:
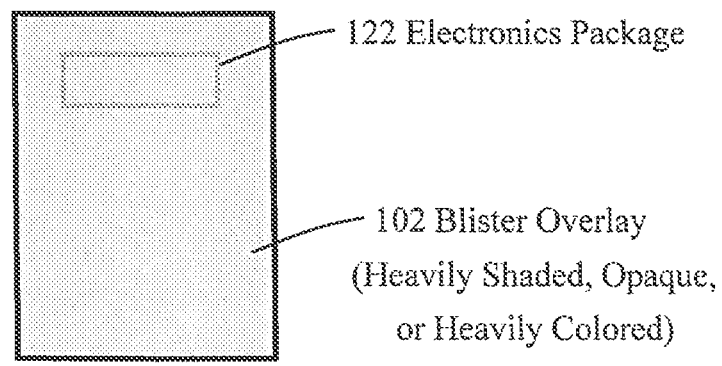

FIG. 10 is an illustration of a blister overlay 102 that has changed to be heavily shaded, opaque, or heavily colored, indicating that the medication contained within the blister pack 104 has expired. In this manner, there is a clear indication to the user that the medication contained within the smart pack having the blister overlay 102 has either a diminished efficacy or may be dangerous to take.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed:

1. An apparatus comprising:
    an overlay configured for operative attachment to a blister pack, the blister pack configured to dispense medication from each of a plurality of blister pockets configured to contain the medication, the overlay comprising:
        a plurality of geometric pattern conductors disposed on the overlay, each of the plurality of geometric pattern conductors aligned with a corresponding one of the plurality of blister pockets when the overlay is operatively attached to the blister pack so that at least a portion of the geometric pattern conductors are broken when the medication is removed from the corresponding one of the plurality of blister pockets creating an open circuit in the geometric pattern conductors,
        a plurality of connecting conductors disposed on the overlay that are electrically coupled to the plurality of geometric pattern conductors and configured to detect the open circuit in the plurality of geometric pattern conductors and identify which of the plurality of geometric pattern conductors has been broken, wherein the plurality of connecting conductors interconnect at least some of the plurality of geometric pattern conductors with one another, and processing and storage circuitry disposed on the overlay configured to detect the open circuit and store a time when the open circuit is detected, to create adherence data.

2. The apparatus of claim 1, further comprising:
communication circuitry disposed on the overlay and electrically coupled to the processing and storage circuitry and configured to communicate the adherence data to a server accessible to authorized individuals.

3. The apparatus of claim 2, wherein the plurality of connecting conductors are formed from conductive ink.

4. The apparatus of claim 3, wherein the plurality of geometric pattern conductors have a zigzag geometric pattern over each of the plurality blister pockets.

5. The apparatus of claim 3, wherein the plurality of connecting conductors are configured in columns and rows to individually identify which of the plurality of geometric pattern conductors that have been broken.

6. The apparatus of claim 1, wherein the medication is a solid medication, a jell medication, or a liquid medication.

7. The apparatus of claim 1, further comprising an automated dispenser configured to dispense the blister pack, the automated dispenser comprising:
communication electronics disposed in the automated dispenser that receives prescriptions for the medication and receives data identifying the medication from the processing and storage circuitry and the communication circuitry of the overlay; and
a processor configured to generate control signals that control:
a card reader that reads debit and credit cards,
a display screen to prompt the user,
a labeler that generates a label containing information identifying a patient taking the medication and instructions for taking the medication, and
a dispenser that dispenses the medication.

8. The apparatus of claim 7, wherein the automated dispenser further comprises a biometric reader for identifying the user of the automated dispenser.

9. The apparatus of claim 1, further comprising a communication system operable with the overlay and configured to communicate adherence data, indicating adherence by a patient to a medication schedule, the communication system comprising a communicator, communicably coupled to the processing and storage circuitry and configured to receive the adherence data from the processing and storage circuitry and transmit the adherence data to a network for storage and access by authorized individuals.

10. The apparatus of claim 9, wherein the authorized individuals comprise an insurance company that generates patient accountability data to score patients, or a pharmacy that generates patient accountability data to score patients, or a healthcare provider that generates patient accountability data to score patients, or law enforcement.

11. The apparatus of claim 9, wherein the communicator is communicably coupled to the processing and storage circuitry via a near field communication protocol.

\* \* \* \* \*